United States Patent [19]

Lesher et al.

[11] 4,432,981
[45] Feb. 21, 1984

[54] 2-(PYRIDINYL OR HYDROXYPHENYL)-8-SUBSTITUTED PYRIDO[2,3-D]PYRIMIDIN-5(8H)-ONES

[75] Inventors: George Y. Lesher, Schodack; Baldev Singh; Stanley C. Laskowski, both of East Greenbush, all of N.Y.

[73] Assignee: Sterling Drug Inc., New York, N.Y.

[21] Appl. No.: 439,361

[22] Filed: Nov. 5, 1982

[51] Int. Cl.$^3$ .................. C07D 487/04; A61K 31/505
[52] U.S. Cl. ..................................... 424/251; 544/279; 544/329; 542/420
[58] Field of Search .......................... 544/279; 424/251

[56] References Cited

U.S. PATENT DOCUMENTS

| | | | |
|---|---|---|---|
| 3,320,257 | 5/1967 | Lesher | 544/279 |
| 3,642,797 | 2/1972 | Lesher | 544/282 |
| 3,673,184 | 6/1972 | Minami et al. | 544/279 |
| 3,770,742 | 11/1973 | Matsumoto et al. | 544/279 |
| 3,873,545 | 3/1975 | Osselaere et al. | 544/279 |
| 3,992,380 | 11/1976 | Lesher et al. | 544/279 |
| 4,018,770 | 4/1977 | Lesher et al. | 424/251 |

OTHER PUBLICATIONS

Matsumoto et al., [Japanese Kokai 78 18,600, published Feb. 20, 1978; C.A. 89, 24,351d (1978)].

*Primary Examiner*—Donald G. Daus
*Assistant Examiner*—S. A. Gibson
*Attorney, Agent, or Firm*—Robert K. Bair; B. Woodrow Wyatt; Paul E. Dupont

[57] ABSTRACT

2-Q-6-Q'-8-R-pyrido[2,3-d]pyrimidin-5(8H)-ones (I), where Q is 4(or 3)-hydroxyphenyl, 4(or 3)-methoxyphenyl, 4(or 3)-pyridinyl or 4(or 3)-pyridinyl having one or two lower-alkyl substituents, R' is hydrogen or alkyl having one to four carbon atoms, Q is hydrogen, amino or nitro, and R is alkyl having from one to four carbon atoms, $CH(C_2H_5)_2$, $(CH_2)_n$=$CHCH_2$ where n is 1 or 2, or Y-Z where Y is alkylene having from two to four carbon atoms and having its connecting linkages on different carbon atoms and Z is hydroxy, $OR_1$ or $NR_1R_2$ where $R_1$ and $R_2$ are each methyl or ethyl, or acid-addition salts thereof, and their preparation are shown. Also shown is the cardiotonic use of I where Q is 4(or 3)-hydroxyphenyl, 4(or 3)-pyridinyl or 4(or 3)-pyridinyl having one or two lower-alkyl substituents and Q' is hydrogen or amino.

16 Claims, No Drawings

2-(PYRIDINYL OR HYDROXYPHENYL)-8-SUBSTITUTED PYRIDO[2,3-D]PYRIMIDIN-5(8H)-ONES

BACKGROUND OF THE INVENTION (a) Field of the Invention

This invention relates to 2-(pyridinyl or hydroxyphenyl)8-substituted-pyrido[2,3-d]pyrimidin-5(8H)-ones, their preparation and their use as cardiotonics.

(b) Description of the Prior Art

Lesher and Singh [U.S. Pat. No. 3,992,380, issued Nov. 16, 1976] show as antibacterial agents, 5,8-dihydro-8-(lower-alkyl)-5-oxo-2-Q-4-$R_2$-6-Z-pyrido[2,3-d]pyrimidines where Z is carboxy or lower-carbalkoxy, $R_2$ is hydrogen or lower-alkyl and Q is 4(or 3)-pyridinyl or 4(or 3)-pyridinyl having one or two lower-alkyl substituents. Said antibacterial agents are prepared by heating di-(lower-alkyl) N-(2-Q-6-$R_2$-4-pyrimidinyl)aminomethylenemalonate to produce 5,8-dihydro-5-oxo-2-Q-4-$R_2$-6-(lowercarbalkoxy)-pyrido[2,3-d]pyrimidine where Q and $R_2$ are as defined above, reacting the latter with a lower-alkylating agent to produce the corresponding 8-(lower-alkyl) compound and hydrolyzing this compound to produce the 6-carboxy derivative.

Lesher and Singh [U.S. Pat. No. 4,018,770, issued Apr. 19, 1977] disclose and claim, inter alia, cyclic alkylidenyl N-[2-(pyridinyl)-4-pyrimidinyl]aminomethylenemalonate, e.g., isopropylidenyl N-[2-(4-pyridinyl)-4-pyrimidinyl]aminomethylenemalonate, alternatively named 2,2-dimethyl-5-<{[2-(4-pyridinyl)-4-pyrimidinyl]amino}methyl>1,3-dioxane-2,4-dione, which are used herein as intermediates.

Osselaere et al. [U.S. Pat. No. 3,873,545, issued Mar. 25, 1975], disclose, inter alia, 2-(3-pyridinyl or 4-pyridinyl)-3,4-dihydropyrido[2,3-d]pyrimidin-4-one as having spasmolytic and diuretic activities.

Matsumoto et al [Japanese Kokai 78 18,600, published Feb. 20, 1978; C.A. 89, 24,351d (1978)] show 8-ethyl-2-(1-piperazinyl)pyrido[2,3-d]pyrimidin-5-one hydrochloride as having analgesic activity in mice and antiinflammatory activity in rats.

Lesher [U.S. Pat. No. 3,642,797, issued Feb. 15, 1972] shows the preparation of a 4H-pyrido[1,2-a]pyrimidin-4-one by heating a cyclic alkylidenyl 2-pyridinylaminomethylenemalonate and also the preparation of a 4-hydroxyquinoline by heating a cyclic alkylidenyl anilinomethylenemalonate as well as the preparation of a 4-hydroxyquinoline by heating an aniline with a mixture of a trialkyl orthoformate and a cyclic alkylidenyl malonate.

SUMMARY OF THE INVENTION

In a composition of matter aspect, the invention resides in 2-Q-4-R'-6-Q'-8-R-pyrido[2,3-d]pyrimidin-5(8H)-ones (I), useful as cardiotonic agents and/or as intermediates, where Q, Q' R and R' are defined hereinbelow.

A composition aspect of the invention resides in the cardiotonic composition for increasing cardiac contractility, said composition comprising a pharmaceutically acceptable carrier, and as the active component thereof, a cardiotonically effective amount of said 2-Q-4-R'-6-Q'-8-R-pyrido[2,3-d]pyrimidin-5(8H)-one (I), where Q, Q', R and R' are defined hereinbelow.

A method aspect of the invention resides in the method for increasing cardiac contractility in a patient requiring such treatment which comprises administering to said patient a medicament comprising a pharmaceutically acceptable carrier and, as the active component, a cardiotonically effective amount of said 2-Q-4-R'-6-Q'-8-R-pyrido[2,3-d]pyrimidin-5(8H)-one.

The invention in a process aspect resides in the process which comprises heating cyclic alkylidenyl N-(2-Q-6-R'-4-pyrimidinyl)aminomethylenemalonate (II) to produce 2-Q-4-R'-pyrido[2,3-d]pyrimidin-5(8H)-one (III) and reacting III with an ester of the formula R-An (IV), where Q, R, R' and An are defined below.

The invention in another process aspect resides in the process which comprises nitrating 2-Q-4-R'-8-R-pyrido[2,3-d]pyrimidin-5(8H)-one (I where Q' is hydrogen) to produce 2-Q-4-R'-6-nitro-8-R-pyrido[2,3-d]pyrimidin-5(8H)-one (I where Q' is $NO_2$) and reacting the 6-nitro compound with a reducing agent to produce 2-Q-4-R'-6-amino-8-R-pyrido[2,3-d]pyrimidin-5(8H)-one (I where Q' is amino).

DETAILED DESCRIPTION INCLUSIVE OF PREFERRED EMBODIMENTS

A composition of matter aspect of the invention resides in a 2-Q-4-R'-6-Q'-8-R-pyrido[2,3-d]pyrimidin-5(8H)-one having formula I

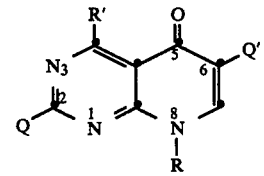

or acid-addition salt thereof, where Q is 4(or 3)-hydroxyphenyl, 4(or 3)-methoxyphenyl, 4(or 3)-pyridinyl or 4(or 3)-pyridinyl having one or two lower-alkyl substituents, R' is hydrogen or alkyl having from one to four carbon atoms, Q' is hydrogen, nitro or amino, and R is alkyl having from one to four carbon atoms, $CH(C_2H_5)_2$, $(CH_2)_nCH=CH_2$ where n is 1 or 2, or Y—Z where Y is alkylene having from two to four carbon atoms and having its connecting linkages on different carbon atoms and Z is hydroxy, $OR_1$ or $NR_1R_2$ where $R_1$ and $R_2$ are each methyl or ethyl. The compounds of formula I where Q' is hydrogen or amino and Q is as defined above excluding 4(or 3)-methoxyphenyl are useful as cardiotonics, as determined by standard pharmacological evaluation procedures. The compounds of formula I where Q' is nitro and Q is 4(or 3)-methoxyphenyl are useful as intermediates for preparing the cardiotonics of formula I respectively where Q' is amino and Q is 4(or 3)-hydroxyphenyl. Preferred embodiments are those of formula I where Q' is hydrogen or amino, R' is hydrogen or methyl, Q is 4(or 3)-pyridinyl and R is ethyl, n-propyl, n-butyl, allyl, 3-butenyl and 1-ethylpropyl, i.e., $CH(C_2H_5)_2$.

A composition aspect of the invention resides in a cardiotonic composition for increasing cardiac contractility, said composition comprising a pharmaceutically acceptable carrier and, as the active component thereof, a cardiotonically effective amount of the compound of formula I where R and R' are defined as in formula I, Q' is amino or hydrogen and Q is 4(or 3)-hydroxyphenyl, 4(or 3)-pyridinyl or 4(or 3)-pyridinyl having one or two lower alkyl substituents, or pharmaceutically acceptable acid-addition salt thereof. Preferred embodiments of this composition aspect of the invention are those where the active component is the compound of formula I where Q is 4(or 3)-pyridinyl, R' is hydrogen or methyl, Q' is hydrogen or amino and R is ethyl, n-propyl, n-butyl, allyl, 3-butenyl and 1-ethylpropyl.

A method aspect of the invention resides in the method for increasing cardiac contractility in a patient requiring such treatment which comprises administering orally or parenterally in a solid or liquid dosage form to such patient a composition comprising a pharmaceutically acceptable carrier and, as active component thereof, a cardiotonically effective amount of the compound of formula I where R and R' are defined as in formula I, Q' is amino or hydrogen and Q is 4(or 3)-hydroxyphenyl, 4(or 3)-pyridinyl or 4(or 3)-pyridinyl having one or two lower-alkyl substituents, or pharmaceutically acceptable salt thereof. Preferred embodiments of this method aspect of the invention are those where the active component is the same as the active component of the preferred composition embodiments described in the immediately preceding paragraph.

A process aspect of the invention resides in the process for producing the compound of formula I where Q' is hydrogen which comprises heating a lower-cyclicalkylidenyl N-(2-Q-6-R'-4-pyrimidinyl)aminomethylenemalonate of the formula II

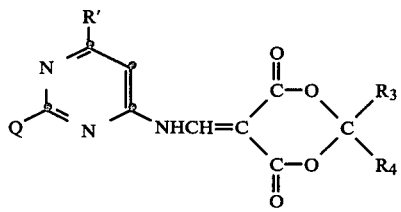

to produce a 2-Q-4-R'-pyrido[2,3-d]pyrimidin-5(8H)-one of the formula III

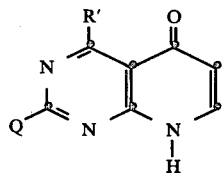

and reacting the compound of formula III or alkali or alkaline earth metal salt thereof with an alkylating agent of the formula R-An (IV) to produce the compound of formula I where Q' is hydrogen, where in formulas II, III and IV R' and R are defined as in formula I, Q is 4(or 3)-methoxyphenyl, 4(or 3)-pyridinyl or 4(or 3)-pyridinyl having one or two lower-alkyl substituents, $R_3$ and $R_4$ are each lower-alkyl having from one to four carbon atoms and An is a leaving group corresponding to the anion of a strong inorganic acid of an organic sulfonic acid, and reacting the compound of formula I where Q' is hydrogen and Q is 4(or 3)-methoxyphenyl with an agent capable of converting methoxyphenyl to hydroxyphenyl. A preferred embodiment of this process aspect of the invention utilizes in the first step the compound of formula II where $R_3$ and $R_4$ are each methyl, R' is hydrogen or methyl and Q is 4(or 3)-pyridinyl, and using in the second step an alkali metal salt of the compound of formula III and R-An where R is ethyl, n-propyl, n-butyl, allyl, 3-butenyl and 1-ethylpropyl and An is chloride, bromide, iodide or sulfate.

Another process aspect of the invention resides in the process which comprises reacting 2-Q-4-R'-8-R-pyrido[2,3-d]pyrimidin-5(8H)-one (I where Q' is hydrogen) with a nitrating agent to produce 2-Q-4-R'-6-nitro-8-R-pyrido[2,3-d]pyrimidin-5(8H)-one (I where Q' is nitro) and reducing said 6-nitro compound to produce the corresponding 2-Q-4-R'-6-amino-8-R-pyrido[2,3-d]pyrimidin-5(8H)-one (I where Q' is amino), where R' and R have the meanings given above for formula I and Q is 4(or 3)-pyridinyl or 4(or 3)-pyridinyl having one or two lower-alkyl substituents. Preferred embodiments of this process aspect of the invention result in the preparation of the 2-Q-4-R'-6-amino-8-R-pyrido[2,3-d]pyrimidin-5(8H)-ones where Q is 4(or 3)-pyridinyl, R' is hydrogen or methyl and R is ethyl, n-propyl, n-butyl, allyl, 3-butenyl and 1-ethylpropyl.

The terms "lower-alkyl", as used herein as one or two substituents of (4 or 3)-pyridinyl, and having from one to four carbon atoms", as used herein, e.g., as the one of the meanings for R or as the meaning for R', $R_3$ or $R_4$ means alkyl radicals having from one to four carbon atoms which can be arranged as straight or branched chains, illustrated by methyl, ethyl, n-propyl, isopropyl, n-butyl, 2-butyl or isobutyl.

Illustrative of Q in formulas I, II or III where Q is 4- or 3-pyridinyl having one or two lower-alkyl substituents are the following: 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl), 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diethyl-3-pyridinyl, 2,6-diisopropyl-4-pyridinyl, and the like.

The compounds of the invention having formula I are useful both in the free base and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, where combined with the free base, pharmaceutically acceptable salts, that is, salts whose anions are relatively innocuous to the animal organism in pharmaceutical doses of the salts, so that the beneficial cardiotonic properties inherent in the free base form of the cardiotonically active compounds of the invention are not vitiated by side effects ascribable to the anions. In practicing the invention, it is convenient to use the free base form; however, appropriate pharmaceutically acceptable salts within the scope of the invention are those derived from mineral acids such as hydrochloric acid, sulfuric acid, phosphoric acid and sulfamic acid; and organic acids such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compounds of formula I are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said basic compounds are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same.

The conversion of lower-cyclic-alkylidenyl N-(2-Q-6-R'-4-pyrimidinyl)aminomethylenemalonate (II) to 2-Q-4-R'-pyrido[2,3-d]pyrimidin-5(8H)-one (III) is carried out by heating II in an inert solvent at about 225°–300° C., preferably at about 240°–270° C. Such solvents include mineral oil, diethyl phthalate, dibenzyl ether, the eutectic mixture of diphenyl and diphenyl ether (DOWTHERM ® A), and the like.

Preparation of the intermediate lower-cyclic-alkylidenyl N-(2Q-6-R'-4-pyrimidinyl)aminomethylenemalonates is shown in said Lesher and Singh U.S. Pat. No. 4,018,770.

The reaction of 2-Q-4-R'-pyrido[2,3-d]pyrimidin-5(8H)-one (III) with an alkylating agent of the formula R-An to produce 2-Q-4-R'-8-R-pyrido[2,3-d]pyrimidin-5(8H)-one (I where Q' is hydrogen and Q is 4(or 3)-methoxyphenyl, 4(or 3)-pyridinyl or 4(or 3)-pyriidnyl having one or two lower-alkyl substituents) is carried out preferably by reacting an alkali metal salt of III with a slight excess of R-An (IV), preferably in an aprotic solvent such as dimethylformamide, where An is a leaving group corresponding to the anion of a strong inorganic acid or an organic sulfonic acid, e.g., bromide, iodide, sulfate, chloride, methanesulfonate, ethanesulfonate, benzenesulfonate, para-toluenesulfonate, and the like; chloride, bromide, iodide and sulfate are preferred because of their ready availability. The reaction is preferably run by first mixing the reactants at room temperature and then heating the reaction mixture at about 75° to 125° C., preferably about 90° to 110° C. The reaction is conveniently run by heating the reactants on a steam bath. The reaction also can be run by forming the alkali or alkaline earth metal salt of III in situ, that is, by mixing III, R-An (IV), solvent and an acid-acceptor such as sodium hydroxide, potassium hydroxide, calcium hydroxide, barium hydroxide, sodium carbonate, potassium carbonate, sodium ethoxide, potassium methoxide, sodium amide, sodium hydride, lithium hydride, calcium hydride, and the like. While the reaction is preferably run in the presence of an aprotic solvent such as dimethylformamide, dioxane, dimethyl sulfoxide, tetramethylurea, dimethylacetamide, hexamethylphosphortriamide, N-methylpyrrolidine, and the like, alternatively it can be run in other solvents such as a lower-alkanol, acetone or a mixture of solvents, e.g., a mixture of water and a lower-alkanol such as methanol, ethanol, isopropyl alcohol, and the like.

The conversion of the compounds of formula I where Q is 4(or 3)-methoxyphenyl to the compounds of formula I where Q is 4(or 3)-hydroxyphenyl is readily achieved by conventional means as illustrated hereinbelow.

The nitration of 2-Q-4-R'-8-R-pyrido[2,3-d]pyrimidin-5(8H)-one (I where Q' is hydrogen and Q is 4(or 3)-pyridinyl or 4(or 3)-pyridinyl having one or two lower-alkyl substituents) to produce the corresponding 2-Q-4-R'-6-nitro-8-R-pyrido[2,3-d]pyrimidin-5(8H)-one (I where Q' is nitro) is carried out by heating I where Q' is hydrogen up to about 100° C. with a nitrating agent such as a mixture of concentrated and/or fuming sulfuric acid and fuming nitric acid, a mixture of potassium nitrate and concentrated sulfuric acid, or other known nitrating agents.

The preparation of the 2-Q-4-R'-6-amino-8-R-pyrido[2,3-d]pyrimidin-5(8H)-one where Q is 4(or 3)-methoxy or 4(or 3)-hydroxyphenyl can be prepared from the corresponding 6-carbethoxy compound [prepared by the procedure described in said Lesher and Singh U.S. Pat. No. 3,992,380] by successive conversions using conventional means first to the corresponding 6-carbamyl compound and then to the 6-amino compound.

The reduction of said 6-nitro compound (I where Q' is nitro) to produce the corresponding 6-amino compound (I where Q' is amino) is carried out with an agent capable of reducing nitro to amino, either by catalytic hydrogenation using Pd/C, $PtO_2$ or Raney Ni catalyst or by chemical reduction, e.g., reduced iron, zinc or iron plus hydrochloric acid, stannous chloride and hydrochloric acid, and the like.

The following examples will further illustrate the invention without, however, limiting it thereto.

A. LOWER-CYCLIC-ALKYLIDENYL N-(2-Q-6-R'-4-PYRIMIDINYL)-AMINOMETHYLENEMALONATES

These compounds and their preparation are generically shown and claimed in said U.S. Pat. No. 4,018,770, issued Apr. 19, 1977. Specifically shown therein (Example B-21) is the reaction of 2-(4-pyridinyl)-4-pyrimidinylamine [same as 4-amino-2-(4-pyridinyl)-pyrimidine] with cyclic isopropylidenyl malonate and triethyl orthoformate in refluxing toluene in the presence of p-toluenesulfonic acid to produce 2,2-dimethyl-5-<[2-(4-pyridinyl)-4-pyrimidinyl]amino methyl>-1,3-dioxane-2,4-dione, which is alternatively and preferably named herein as cyclic isopropylidenyl N-[2-(4-pyridinyl)-4-pyrimidinyl]aminomethylenemalonate. Alternatively, these compounds can be prepared by first reacting lower-cyclic-alkylidenyl malonate with a tri-(lower-alkyl) orthoformate to prepare lower-cyclic-alkylidenyl lower-alkoxymethylenemalonate which is then reacted with 2-Q-6-R'-4-pyrimidinamine to produce lower-cyclic-alkylidenyl N-[2-Q-6-R'-4-pyrimidinyl]aminomethylene-malonate, as illustrated hereinbelow.

A-1. Isopropylidenyl N-[2-(4-pyridinyl)-4-pyrimidinyl]aminomethylenemalonate—A mixture containing 33.8 g of 4-(4-pyridinyl)-2-pyrimidinamine and 2.3 liters of methanol was refluxed with stirring for 30 minutes and the mixture was filtered through diatomaceous earth. To the filtrate was added portionwise with stirring 36.5 g of cyclic isopropylidenyl methoxymethylenemalonate and the reaction mixture was refluxed with stirring for 10 minutes and then cooled in an ice bath. The precipitated solid was collected, washed with a small quantity of cold methanol and dried at 65° C. in vacuo to produce 58.4 g of isopropylidenyl N-[2-(4-pyridinyl)-4-pyrimidinyl]-aminomethylenemalonate, m.p., 250°–251° C.

The above intermediate cyclic isopropylidenyl methoxymethylenemalonate was prepared as follows: a stirred solution containing 72 g of cyclic isopropylidenyl malonate and 26.5 g of trimethyl orthoformate was heated on a steam bath for two hours and cooled in an ice bath. Separated solid was collected, washed with n-hexane dried in vacuo at 50° C., recrystallized from methanol (total volume of about 325 ml) washed with a small quantity of cold methanol and dried in vacuo at 60° C. to yield 43.4 g of cyclic isopropylidenyl methoxymethylenemalonate, m.p. 142°–144° C.

A-2. Cyclic isopropylidene N-[2-(3-pyridinyl)-4-pyrimidinyl]aminomethylenemalonate, m.p. 245°–246° C., 4.6 g, was prepared following the procedure described in Example A-1 using 5.1 g of 4-(3-pyridinyl)-2-pyrimidinamine, 5.5 g of cyclic isopropylidenyl methoxymethylenemalonate and 150 ml of methanol.

A-3. Cyclic isopropylidene N-[2-(4-methoxyphenyl)-4-pyrimidinyl]aminomethylenemalonate, m.p. 232°–233° C., 6.5 g, was prepared following the procedure described in Example A-1 using 4.02 g of 4-(4-methoxyphenyl)-2-pyrimidinamine, 3.72 g of cyclic isopropylidenyl methoxymethylenemalonate and 50 ml of methanol.

The above intermediate 2-(4-methoxyphenyl)-4-pyrimideneamine was prepared as follows: A slurry containing 81 g of 4-methoxybenzamidine hydrochloride, 24 g of sodium methoxide and 200 ml of methanol was stirred for 15 minutes, filtered and the filtrate concentrated in vacuo on a steam bath. To the residue was added β-ethoxyacrylonitrile (same as ethoxymethyleneacetonitrile) and the solution was heated at 100°–115° C. for 2 and ½ hours and poured into water. The solid was collected, washed with water, air-dried, and crystallized from ether-n-hexane to yield 85 g of 2-(4-methoxyphenyl)-4-pyrimidinamine, m.p. 102°–104° C.

Following the procedure described in Example A-1 using in place of 2-(4-pyridinyl)-4-pyrimidinamine a molar equivalent quantity of the corresponding 2-Q-6-R'-4-pyrimidinamine, it is contemplated that the following cyclic isopropylidenyl N-(2-Q-6-R'-4-pyrimidinyl)-aminomethylenemalonates of Examples A-4 through A-9 can be obtained.

A-4. Cyclic isopropylidenyl N-[2-(4-pyridinyl)-6-methyl-4-pyrimidinyl]aminomethylenemalonate, using 2-(4-pyridinyl)-6-methyl-4-pyrimidinamine.

A-5. Cyclic isopropylidenyl N-[2-(2-methyl-4-pyridinyl)-6-pyrimidinyl]aminomethylenemalonate, using 2-(2-methyl-4-pyridinyl)-4-pyrimidinamine.

A-6. Cyclic isopropylidenyl N-[2-(3-methyl-4-pyridinyl)-6-pyrimidinyl]aminomethylenemalonate, using 2-(3-methyl-4-pyridinyl)-4-pyrimidinamine.

A-7. Cyclic isopropylidenyl N-[2-(2-ethyl-4-pyridinyl)-6-pyrimidinyl]aminomethylenemalonate, using 2-(2-ethyl-4-pyridinyl)-4-pyrimidinamine.

A-8. Cyclic isopropylidenyl N-[2-(2,6-dimethyl-4-pyridinyl)-6-pyrimidinyl]aminomethylenemalonate, using 2-(2,6-dimethyl-4-pyridinyl)-4-pyrimidinamine.

A-9. Cyclic isopropylidenyl N-[2-(4-pyridinyl)-6-n-propyl-4-pyrimidinyl]aminomethylenemalonate, using 2-(4-pyridinyl)-6-n-propyl-4-pyrimidinamine.

B.
2-Q-4-R'-PYRIDO[2,3-d]PYRIMIDIN-5(8H)-ONES

B-1. 2-(4-Pyridinyl)pyrido[2,3-d]pyrimidin-5(8H)-one—To a 600 ml portion of a eutectic mixture of diphenyl and diphenyl ether was added in four portions 15.6 g of isopropylidenyl N-[2-(4-pyridinyl)-4-pyrimidinyl]aminomethylenemalonate and the resulting reaction mixture was heated at about 245° C. for about five minutes and then allowed to cool to room temperature. The solid that separated was collected, washed with n-hexane, slurried with 600 ml of refluxing chloroform for about two hours, filtered, washed with chloroform and dried at 65° C. in vacuo to produce 6.1 g of 2-(4-pyridinyl)pyrido[2,3-d]pyrimidin-5(8H)-one. This 6.1 g portion of product was combined with another 5.2 g of the same compound obtained in another run and the combination was dissolved in 300 ml of boiling dimethylformamide, the hot solution treated with decolorizing charcoal and filtered, and the filtrate also treated with decolorizing charcoal and filtered. The filtrate was cooled in an ice bath to precipitate the product. The product was collected, washed with n-hexane and dried at 65° C. in vacuo to produce 6.2 g of 2-(4-pyridinyl)-pyrido[2,3-d]pyrimidin-5(8H)-one, m.p. >350° C.

B-2. 2-(3-Pyridinyl)pyrido[2,3-d]pyrimidin-5(8H)-one, 5.15 g, m.p. >350° C., was prepared following the procedure described in Example B-1 using 9.35 g of cyclic isopropylidenyl N-[2-(3-pyridinyl)-4-pyrimidinyl]aminomethylenemalonate, 550 ml of a eutectic mixture of diphenyl and diphenylether, and a refluxing temperature of 250° C.

B-3. 2-(4-Methoxyphenyl)pyrido[2,3-d]pyrimidin-5(8H)-one, 5.8 g, m.p. 345°–346° C., was prepared following the procedure described in Example B-1 using 11.6 g of cyclic isopropylidenyl N-[2-(4-methoxyphenyl)-4-pyrimidinyl]aminomethylenemalonate, 500 ml of a eutectic mixture of diphenyl and diphenyl ether and a refluxing temperature of 250° C.

Following the procedure described in Example B-1 using in place of isopropylidenyl N-[2-(4-pyridinyl)-4-pyrimidinyl)aminomethylenemalonate a molar equivalent quantity of the corresponding cyclic isopropylidenyl N-(2-Q-6-R'-4-pyrimidinyl)aminomethylenemalonate, it is contemplated that the following 2-Q-4-R'-pyrido[2,3-d]pyrimidin-5-(8H)-ones of Example B-4 through B-9 can be obtained.

B-4. 2-(4-Pyridinyl)-4-methylpyrido[2,3-d]pyrimidin-5(8H)-one, using cyclic isopropylidenyl N-[2-(4-pyridinyl)-6-methyl-4-pyrimidinyl]aminomethylenemalonate.

B-5. 2-(2-Methyl-4-pyridinyl)pyrido[2,3-d]pyrimidin-5(8H)-one, using cyclic isopropylidenyl N-[2-(2-methyl-4-pyridinyl)-6-pyrimidinyl]aminomethylenemalonate.

B-6. 2-(3-Methyl-4-pyridinyl)pyrido[2,3-d]pyrimidine-5(8H)-one, using cyclic isopropylidinyl N-[2-(3-methyl-4-pyridinyl)-6-pyrimidinyl]aminomethylenemalonate.

B-7. 2-(2-Ethyl-4-pyridinyl)pyrido[2,3-d]pyrimidin-5(8H)-one, using cyclic isopropylidenyl N-[2-(2-ethyl-4-pyridinyl)-6-pyrimidinyl]aminomethylenemalonate.

B-8. 2-(2,6-Dimethyl-4-pyridinyl)pyrido[2,3-d]-pyrimidin-5(8H)-one, using cyclic isopropylidenyl N-[2-(2,6-dimethyl-4-pyridinyl)-6-pyrimidinyl]aminomethylenemalonate.

B-9. 2-(4-Pyridinyl)-6-n-propylpyrido[2,3-d]pyrimidin-5(8H)-one, using cyclic isopropylidenyl N-[2-(4-pyridinyl]-6-n-propyl-4-pyrimidinyl)aminomethylenemalonate.

C.
2-Q-4-R'-6-Q'-8-R-PYRIDO[2,3-d]PYRIMIDIN-5-(8H)-ONES

C-1. 8-Ethyl-2-(4-pyridinyl)pyrido[2,3-d]pyrimidin-5(8H)-one—A mixture containing 12.7 g of 2-(4-pyridinyl)-pyrido[2,3-d]pyrimidin-5(8H)-one, 2.74 g of 50% sodium hydride in mineral oil and 300 ml of dimethylformamide was stirred at room temperature until evolution of hydrogen ceased. The mixture was heated gently with stirring on a steam bath for 30 minutes, one drop diisopropylamine was added followed by 100 mg of sodium hydride and gentle heating with stirring was continued for another 45 minutes. The mixture was then cooled to room temperature and to it was added dropwise with stirring at room temperature 8.85 g of ethyl iodide. The reaction mixture was stirred at room temperature for three hours and then heated gently with stirring on a steam bath for 30 minutes. The solvent was then distilled off in vacuo and the residue was shaken well with a mixture of water and chloroform. The water layer was extracted several times with chloroform and the chloroform extracts were combined with the chloroform layer. The combined chloroform solution was dried over anhydrous sodium sulfate, the mixture filtered, and the filtrate treated with decolorizing charcoal and filtered. The chloroform was distilled off in vacuo and the remaining 12 g of solid residue was dissolved in 300 ml of hot isopropyl alcohol, the hot alcohol solution treated with decolorizing charcoal and filtered. The filtrate was concentrated to a volume of about 150 ml and cooled. The precipitated solid was collected, washed with a small quantity of cold isopropyl alcohol, and dried at 65° C. in vacuo to produce 6.8 g of 8-ethyl-2-(4-pyridinyl)pyrido[2,3-d]pyrimidin-5(8H)-one, m.p. 200°–202° C. Additional product was obtained from the mother liquor.

Acid-addition salts of 8-ethyl-2-(4-pyridinyl)-pyrido[2,3-d]pyrimidin-5(8H)-one are conveniently prepared by adding to a mixture of 1 g of 8-ethyl-2-(4-pyridinyl)-pyrido[2,3-d]pyrimidin-5(8H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 8-ethyl-2-(4-pyridinyl)pyrido[2,3-d]pyrimidin-5(8H)-one and the appropriate acid, e.g., lactic acid or hydrochloric acid, to prepare respectively the lactate or hydrochloride salt of 8-ethyl-2-(4-pyridinyl)pyrido[2,3-d]pyrimidin-5(8H)-one in aqueous solution.

C-2. 8-Ethyl-2-(3-pyridinyl)pyrido[2,3-d]pyrimidin-5(8H)-one—A mixture containing 8.7 g of 2-(3-pyridinyl)-pyrido[2,3-d]pyrimidin-5(8H)-one, 1.9 g of 50% sodium hydride in mineral oil and 250 ml of dimethylformamide was stirred at room temperature until evolution of hydrogen ceased. To the mixture was added an additional 50 ml of dimethylformamide and gentle heating was continued on a steam bath for 30 minutes. The mixture was cooled to room temperature and to it was added one drop of diisopropyl amine with stirring followed by an additional 100 mg of sodium hydride. Gentle heating with stirring was continued for another 30 minutes followed by cooling to room temperature. To the mixture was added with stirring at room temperature 6.1 g of ethyl iodide slowly in a fine stream and resulting reaction mixture was stirred at room temperature for three hours and then heated gently with stirring on a steam bath for four hours. The reaction mixture was then distilled in vacuo to remove the solvent and any other volatile materials and the residue was taken up and shaken well with a mixture of chloroform and water. The layers were separated and the chloroform layer was dried over anhydrous sodium sulfate, treated with decolorizing charcoal and filtered, and the filtrate was distilled in vacuo to remove the chloroform. The residue was dissolved in 150 ml of boiling acetonitrile: the resulting hot solution was treated with decolorizing charcoal and filtered; and, the filtrate was concentrated to a volume of 100 ml and cooled to complete precipitation of the product. The product was collected, washed successively with a small quantity of acetonitrile and n-hexane, and dried in vacuo at 65° C. to yield 6.5 g of 8-ethyl-2-(3-pyridinyl)-pyrido[2,3-d]pyrimidin-5(8H)-one, m.p. 195°–196° C.

Acid-addition salts of 8-ethyl-2-(3-pyridinyl)-pyrido[2,3-d]pyrimidin-5(8H)-one are conveniently prepared by adding to a mixture of 1 g of 8-ethyl-2-(3-pyridinyl)-pyrido[2,3-d]pyrimidin-5(8H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 8-ethyl-2-(3-pyridinyl)pyrido[2,3-d]pyrimidin-5(8H)-one and the appropriate acid, e.g., lactic acid or hydrochloric acid, to prepare respectively the lactate or hydrochloride salt of 8-ethyl-2-(3-pyridinyl)pyrido[2,3-d]pyrimidin-5(8H)-one in aqueous solution.

C-3. 8-Ethyl-2-(4-methoxyphenyl)pyrido[2,3-d]pyrimidin-5(8H)-one, 9.1 g, m.p. 220°–223° C., was prepared following the procedure described in Example C-2 in two runs using 6.0 and 12.25 g of starting material, e.g, 2-(4-methoxyphenyl)pyrido[2,3-d]pyrimidin-5(8H)-one, and recrystallizing the combined products from absolute ethanol.

C-4. 8-Ethyl-2-(4-hydroxyphenyl)pyrido[2,3-d]pyrimidin-5(8H)-one—A mixture containing 2.4 g of 8-ethyl-2-(4-methoxyphenyl)pyrido[2,3-d]pyrimidin-5(8H)-one, 8.1 g of anhydrous lithium iodide, 125 ml of collidine and one drop of dicyclohexyl-12-crown-4 was refluxed with stirring for 24 hours and then allowed to cool to room temperature. The reaction mixture was diluted with n-hexane (900 ml) to complete the precipitation of the product. The oily material that separated solidified on standing at room temperature. The solid was collected, washed with n-hexane and then dissolved in water. The water solution and washed with ether, acidified with hydrochloric acid and the resulting mixture was slurried, treated with an excess of sodium bicarbonate and again slurried. The solid was collected, washed with water and dried at 65° C. in vacuo to yield 1.85 g of 8-ethyl-2-(4-hydroxyphenyl)pyrido[2,3-d]pyrimidin-5(8H)-one, m.p. 320°–324° C. This product was combined with 12 g of product obtained in five other runs and the combined material was suspended in about 350 ml of boiling ethanol after which dimethylformamide was added portionwise until dissolution was complete. The hot solution was treated with decolorizing charcoal, filtered, and the filtrate cooled. The separated product was collected, washed with cold ethanol and dried in vacuo at 60° C. to produce 2.6 g of 8-ethyl-2-(4-hydroxyphenyl)pyrido[2,3-d]pyrimidin-5(8H)-one, m.p. 323°–325° C. The filtrate was stripped in vacuo, the solid residue was recrystallized from ethanoldimethylformamide to yield another 0.8 g of product, 8-ethyl-2-(4-hydroxyphenyl)pyrido[2,3-d]pyrimidin-5(8H)-one, m.p. 321°–322° C.

C-5. 8-n-Propyl-2-(4-pyridinyl)pyrido[2,3-d]pyrimidin-5(8H)-one, 4.7 g, m.p. 180°–181° C., was obtained following the procedure described in Example C-2 using 11.2 g of 2-(4-pyridinyl)pyrido[2,3-d]pyrimidin-5(8H)-one, 300 ml of dimethylformamide, 2.4 g of 50% sodium hydride in mineral oil, 8.5 g of n-propyl iodide, a heating period of twelve hours, and recrystallization from isopropyl alcohol using decolorizing charcoal.

C-6. 8-n-Butyl-2-(4-pyridinyl)pyrido[2,3-d]pyrimidin-5(8H)-one, 8.3 g, m.p. 160°–161° C., was obtained following the procedure described in Example C-2 using 13.1 g of 2-(4-pyridinyl)pyrido[2,3-d]pyrimidin-5(8H)-one, 300 ml of dimethylformamide, 2.8 g of 50% sodium hydride in mineral oil, 10.8 g of n-butyl iodide, a heating period of seven hours, and recrystallization from isopropyl alcohol using decolorizing charcoal.

C-7. 8-n-Butyl-2-(3-pyridinyl)pyrido[2,3-d]pyrimidin-5(8H)-one, 5.7 g, m.p. 133°–135° C., was prepared following the procedure described in Example C-2 using 9.3 g of 2-(3-pyridinyl)pyrido[2,3-d]pyrimidin-5(8H)-one, 250 ml of dimethylformamide, 2.0 g of 50% sodium hydride in mineral oil, 7.65 g of n-butyl iodide, a heating period of eight hours, and recrystallization from isopropyl alcohol using decolorizing charcoal.

C-8. 8-n-Butyl-6-nitro-2-(4-pyridinyl)pyrido[2,3-d]pyrimidin-5(8H)-one—To 7.2 g of concentrated sulfuric acid was added, with stirring and cooling keeping the temperature below 30° C., 10.8 ml of fuming sulfuric acid. To the resulting mixture was added 6.0 ml of fuming nitric acid with stirring, and cooling as necessary to keep the temperature below 30° C. To the stirred mixture of acids at room temperature was added 6.6 g of 8-n-butyl-2-(4-pyridinyl)pyrido[2,3-d]pyrimidin-5(8H)-one. The reaction mixture was heated with stirring, gradually raising the temperature to 90° over a twenty minute period and then maintaining the reaction mixture at 90°–95° C. for ten minutes. The reaction mixture was cooled to 30° C. and added to 500 ml of a mixture of ice and water. The resulting mixture was made basic by adding concentrated ammonium hydroxide and the resulting mixture was allowed to stand for one hour. The separated solid was collected, washed with water, dried at 65° C. in vacuo to produce 6.3 g of 8-n-butyl-6-nitro-2-(4-pyridinyl)pyrido[2,3-d]pyrimidin-5(8H)-one, m.p. 240°–241° C. The product was dissolved in 50 ml of boiling dimethylformamide, the solution treated with decolorizing charcoal and filtered, and the filtrate concentrated to a volume of about 30 ml and cooled to complete precipitation of the product. The product was collected, washed with a small quantity of cold ethanol, and dried at 65° C. in vacuo to produce 5.25 g of 8-n-butyl-6-nitro-2-(4-pyridinyl)pyrido[2,3-d]pyrimidin-5(8H)-one, m.p. 241°–243° C.

C-9. 6-Amino-8-n-butyl-2-(4-pyridinyl)pyrido[2,3-d]pyrimidin-5(8H)-one—A stirred mixture containing 400 ml of absolute methanol, 80 ml of water, 1 ml of concentrated hydrochloric acid and 8.6 g of reduced iron was brought to a boil in an 800 ml beaker on a steam bath. The heat was removed and to the mixture was added portionwise with stirring 7.95 g of 8-n-butyl-6-nitro-2-(4-pyridinyl)pyrido[2,3-d]pyrimidin-5(8H)-one and the reaction mixture was then boiled with stirring for 30 minutes. To the reaction mixture was added portionwise 8.0 g of sodium bicarbonate and the resulting mixture was boiled with stirring for an additional 10 minutes, during which time additional absolute ethanol was added intermittently to maintain constant volume. The hot reaction mixture was filtered through diatomaceous earth and the pad washed with hot ethanol. The filtrate was heated in vacuo to remove the solvent and other volatile materials. The residue was taken up in 100 ml of chloroform and the chloroform solution was dried over anhydrous sodium sulfate, the mixture filtered and the filtrate stripped in vacuo to produce 7.3 g of solid, m.p. 193°–195° C. The solid was combined with another 0.9 g of the corresponding solid prepared in another run and the mixture was dissolved in 200 ml of boiling isopropyl alcohol, the volume concentrated to 100 ml and cooled to complete precipitation of the product. The solid was collected, washed with cold isopropyl alcohol and dried at 65° C. in vacuo to produce 7.2 g of 6-amino-8-n-butyl-2-(4-pyridinyl)-pyrido[2,3-d]pyrimidin-5(8H)-one, m.p. 195°–196° C.

Acid-addition salts of 6-amino-8-n-butyl-2-(4-pyridinyl)pyrido[2,3-d]pyrimidin-5(8H)-one are conveniently prepared by adding to a mixture of 1 g of 6-amino-8-n-butyl-2-(4-pyridinyl)pyrido[2,3-d]pyrimidin-5(8H)-one in about 20 ml of aqueous methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively. Also, the acid-addition salt is conveniently prepared in aqueous solution by adding to water with stirring a molar equivalent quantity each of 6-amino-8-n-butyl-2-(4-pyridinyl)pyrido[2,3-d]pyrimidin-5(8H)-one and the appropriate acid, e.g., lactic acid or hydrochloric acid, to prepare respectively the lactate or hydrochloride salt of 6-amino-8-n-butyl-2-(4-pyridinyl)-pyrido[2,3-d]pyrimidin-5(8H)-one in aqueous solution.

C-10. 8-(1-Ethylpropyl)-2-(4-pyridinyl)pyrido[2,3-d]pyrimidin-5(8H)-one, 5.0 g, m.p. 157°–160° C., was prepared following the procedure described in Example C-2 using 11.2 g of 2-(4-pyridinyl)pyrido[2,3-d]pyrimidin-5(8H)-one, 300 ml of dimethylformamide, 2.4 g of 50% sodium hydride in mineral oil, 9.9 g of 3-pentyl iodide, a heating period of 19 hours, and recrystallization from isopropyl acetate using decolorizing charcoal.

C-11. 8-(3-Butenyl)-2-(4-pyridinyl)pyrido[2,3-d]pyrimidin-5(8H)-one, 4.2 g, m.p. 141°–143° C., was prepared following the procedure described in Example C-2 using 8.2 g of 2-(4-pyridinyl)pyrido[2,3-d]pyrimidin-5(8H)-one, 250 ml of dimethylformamide, 1.75 g of 50% sodium hydride in mineral oil, 4.93 g of 3-butenyl bromide, a heating period of 19 hours, recrystallization from isopropyl alcohol using decolorizing charcoal and a second recrystallization from isopropyl alcohol.

C-12. 8-Isopropyl-2-(4-pyridinyl)pyrido[2,3-d]pyrimidin-5(8H)-one, 5.6 g, m.p. 269°–271° C., was prepared following the procedure described in Example C-2 using 11.2 g of 2-(4-pyridinyl)pyrido[2,3-d]pyrimidin-5(8H)one, 300 ml of dimethylformamide, 2.4 g of 50% sodium hydride in mineral oil, 8.5 g of isopropyl iodide, a heating period of 24 hours and two recrystallizations from isopropyl alcohol.

C-13. 8-(2-Methoxyethyl)-2-(4-pyridinyl)pyrido[2,3-d]pyrimidin-5(8H)-one, 4.0 g, m.p. 202°-203° C., was prepared following the procedure described in Example C-2 using 8 g of 2-(4-pyridinyl)pyrido[2,3-d]pyrimidin-5(8H)-one, 250 ml of dimethylformamide, 1.72 g of 50% sodium hydride in mineral oil, 5 g of 2-methoxyethyl bromide, a heating period of 18 hours and two recrystallizations from absolute ethanol.

C-14. 8-Methyl-2-(4-pyridinyl)pyrido[2,3-d]pyrimidin-5(8H)-one, 5.0 g, m.p. 266°-268° C., was prepared following the procedure described in Example C-2 using 12.35 g of 2-(4-pyridinyl)pyrido[2,3-d]pyrimidin-5(8H)-one, 300 ml of dimethylformamide, 2.65 g of 50% sodium hydride in mineral oil, 7.8 g of methyl iodide, a heating period of 30 minutes, and two recrystallizations from ethanol using decolorizing charcoal.

C-15. 8-(2-Hydroxyethyl)-2-(4-pyridinyl)pyrido[2,3-d]pyrimidin-5(8H)-one, 4.7 g, m.p. 250°-252° C., was prepared following the procedure described in Example C-2 using 12.35 g of 2-(4-pyridinyl)pyrido[2,3-d]pyrimidin-5(8H)-one, 300 ml of dimethylformamide, 2.65 g of 50% sodium hydride in mineral oil, 9.5 g of 2-hydroxyethyl iodide, a heating period of seven hours, and recrystallization from absolute ethanol using decolorizing charcoal.

C-16. 8-(3-Hydroxypropyl)-2-(4-pyridinyl)-pyrido[2,3-d]pyrimidin-5(8H)-one, 4.2 g, m.p. 198°-201° C., was prepared following the procedure described in Example C-2 using 10.0 g of 2-(4-pyridinyl)pyrido[2,3-d]pyrimidin-5(8H)-one, 250 ml of dimethylformamide, 2.12 g of 50% sodium hydride in mineral oil, 6.2 g of 3-hydroxypropyl bromide, a heating period of 18 hours, and two recrystallizations from isopropyl alcohol.

C-17. 8-(2-Dimethylaminoethyl)-2-(4-pyridinyl)-pyrido[2,3-d]pyrimidin-5(8H)-one, 4.9 g, m.p. 157°-159° C., was prepared following the procedure described in Example C-2 using 8.0 g of 2-(4-pyridinyl)pyrido[2,3-d]pyrimidin-5(8H)-one, 250 ml of dimethylformamide, 1.72 g of 50% sodium hydride in mineral oil, 3.86 g of 2-dimethylaminoethyl chloride, a heating period of eight hours, and recrystallization from isopropyl acetate using decolorizing charcoal.

Following the procedure described in Example C-2 but using in place of 2-(3-pyridinyl)-pyrido[2,3-d]pyrimidin-5(8H)-one and ethyl iodide corresponding molar equivalent quantities of the appropriate 2-Q-4-R'-pyrido[2,3-d]pyrimidin-5(8H)-one and alkylating agent of the formula R-An, it is contemplated that the corresponding products of Examples C-18 thru C-25 can be obtained.

C-18. 8-Ethyl-4-methyl-2-(4-pyridinyl)pyrido[2,3-d]pyrimidin-5(8H)-one, using 4-methyl-2-(4-pyridinyl)-pyrido[2,3-d]pyrimidin-5(8H)-one and ethyl iodide.

C-19. 8-Ethyl-2-(2-methyl-4-pyridinyl)pyrido[2,3-d]pyrimidin-5(8H)-one, using 2-(2-methyl-4-pyridinyl)-pyrido[2,3-d]pyrimidin-5(8H)-one and ethyl bromide.

C-20. 8-n-Butyl-2-(3-methyl-4-pyridinyl)pyrido[2,3-d]pyrimidin-5(8H)-one and n-butyl bromide.

C-21. 2-(2-Ethyl-4-pyridinyl)-8-n-propylpyrido[2,3-d]pyrimidin-5(8H)-one, using 2-(2-ethyl-4-pyridinyl)-pyrido[2,3-d]pyrimidin-5(8H)-one and n-propyl iodide.

C-23. 8-Ethyl-2-(2,6-dimethyl-4-pyridinyl)pyrido[2,3-d]pyrimidin-5(8H)-one, using 2-(2,6-dimethyl-4-pyridinyl)pyrido[2,3-d]pyrimidin-5(8H)-one and ethyl iodide.

C-24. 8-Ethyl-4-n-propyl-2-(4-pyridinyl)pyrido[2,3-d]pyrimidin-5(8H)-one, using 4-n-propyl-2-(4-pyridinyl)pyrido[2,3-d]pyrimidin-5(8H)-one and ethyl bromide.

C-25. 8-Allyl-2-(4-pyridinyl)pyrido[2,3-d]pyrimidin-5(8H)-one, using 2-(4-pyridinyl)pyrido[2,3-d]pyrimidin-5(8H)-one and allyl bromide.

Following the procedure described in Example C-8 but using in place of 8-n-butyl-2-(4-pyridinyl)-pyrido[2,3-d]pyrimidin-5(8H)-one a molar equivalent quantity of the appropriate 2-Q-4-R'-8-R-pyrido[2,3-d]pyrimidin-5(8H)-one, it is contemplated that the following 6-nitro compounds of Examples C-26 thru C-29 can be obtained.

C-26. 8-Ethyl-6-nitro-2-(2-methyl-4-pyridinyl)-pyrido[2,3-d]pyrimidin-5(8H)-one, using 8-ethyl-2-(2-methyl-4-pyridinyl)pyrido[2,3-d]pyrimidin-5(8H)-one.

C-27. 4-Methyl-6-nitro-8-n-propyl-2-(4-pyridinyl)-pyrido[2,3-d]pyrimidin-5(8H)-one, using 4-methyl-8-n-propyl-2-(4-pyridinyl)pyrido[2,3-d]pyrimidin-5(8H)-one.

C-28. 2-(2-Ethyl-4-pyridinyl)-6-nitro-8-n-propyl-pyrido[2,3-d]pyrimidin-5(8H)one, using 2-(2-ethyl-4-pyridinyl)-8-n-propylpyrido[2,3-d]pyrimidin-5(8H)-one.

C-29. 8-Ethyl-2-(2,6-dimethyl-4-pyridinyl)-6-nitropyrido[2,3-d]pyrimidin-5(8H)-one using 8-ethyl-2-(2,6-dimethyl-4-pyridinyl)pyrido[2,3-d]pyrimidin-5(8H)one.

Following the procedure described in Example C-9 but using in place of 8-n-butyl-6-nitro-2-(4-pyridinyl)-pyrido[2,3-d]pyrimidin-5(8H)-one a corresponding molar equivalent quantity of the corresponding 2-Q-4-R'-6-nitro-8-R-pyrido[2,3-d]pyrimidin-5(8H)-one, it is contemplated that the corresponding 6-amino compounds of Examples C-30 thru C-33 can be obtained.

C-30. 6-Amino-8-ethyl-2-(2-methyl-4-pyridinyl)-pyrido[2,3-d]pyrimidin-5(8H)-one, using 8-ethyl-2-(2-methyl-4-pyridinyl-6-nitropyrido[2,3-d]pyrimidin-5(8H)-one.

C-31. 6-Amino 4-methyl-8-n-propyl-2-(4-pyridinyl)-pyrido[2,3-d]pyrimidin-5(8H)-one, using 4-methyl-6-nitro-8-n-propyl-2-(4-pyridinyl)pyrido[2,3-d]pyrimidin-5(8H)one.

C-32. 6-Amino-2-(2-ethyl-4-pyridinyl)-8-n-propyl-pyrido[2,3-d]pyrimidin-5(8H)-one, using 2-(2-ethyl-4-pyridinyl)-6-nitro-8-n-propylpyrido[2,3-d]pyrimidin-5(8H)one.

C-33. 6-Amino-8-ethyl-2-(2,6-dimethyl-4-pyridinyl)-pyrido[2,3-d]pyrimidin-5(8H)-one, using 8-ethyl-6-nitro-2-(2,6-dimethyl-4-pyridinyl)pyrido[2,3-d]pyrimidin-5(8H)one.

C-34. 8-Ethyl-2-(3-methoxyphenyl)pyrido[2,3-d]pyrimidin-5(8H)-one can be prepared following the procedure described in Example C-2 using in place of 2-(3-pyridinyl)pyrido[2,3-d]pyrimidin-5(8H)-one, a molar equivalent quantity of 2-(3-methoxyphenyl)-pyrido[2,3-d]pyrimidin-5(8H)-one.

C-35. 8-Ethyl-2-(3-hydroxyphenyl)pyrido[2,3-d]pyrimidin-5(8H)-one can be prepared following the procedure described in Example C-4 but using in place of 8-ethyl-2-(4-methoxyphenyl)pyrido[2,3-d]pyrimidin-5(8H)-one, a molar equivalent quantity of the corresponding 8-ethyl-2-(3-methoxyphenyl)pyrido[2,3-d]pyrimidin-5(8H)-one.

The utility of the compounds of formula I where Q' is amino or hydrogen and Q is 4(or 3)-hydroxyphenyl, 4(or 3)-pyridinyl or 4(or 3)-pyridinyl having one or two lower-alkyl substituents of their pharmaceutically acceptable acid-addition salts as cardiotonic agents is demonstrated by their effectiveness in standard pharmacological test procedures, for example, in causing a significant increase in contractile force of the isolated cat or guinea pig atria and papillary muscle and/or in causing a significant increase in the cardiac contractile force in the anesthetized dog with low or minimal changes in heart rate and blood pressure. Detailed descriptions of these test procedures appear in U.S. Pat. No. 4,072,746, issued Feb. 7, 1980.

When tested by said isolated cat or guinea pig atria and papillary muscle procedure, the compounds of the invention or said salts thereof at doses of 3, 10, 30, and/or 100 µg/ml., were found to cause significant increases, that is, greater than 25% (cat) or 30% (g. pig) in papillary muscle force and significant increases, that is greater than 25% (cat) or 30% (g. pig) in right atrial force, while causing a lower percentage increase (about one-half or less than the percentage increase in right atrial force or papillary muscle force) in right atrial rate. Because of the lower control active tensions of guinea pig tissues, the percent change from control values of both rate and force responses is elevated slightly, i.e., 5%. Thus, whereas cardiotonic activity is ascertained with a papillary muscle force or right atrial force increase of 26% and greater in the cat test, corresponding activity in the guinea pig test is designated with a papillary muscle force or right atrial force increase of 31% or greater. For example, illustrative cat papillary muscle and right atrial force increases for a compound of the invention are: 119% and 143% at 100 µg/ml, 105% and 108% at 30 µg/ml, and 58% and 59% at 10 µg/ml for the compound of Example C-1. Further, illustrative guinea pig papillary muscle and right atrial force increases for other compounds of the invention are: 137% and 406% at 100 µg/ml, and 64% and 138% at 30 µg/ml for the compound of Example C-2; 137% and 116% at 30 µg/ml, and 66% and 128% at 10 µg/ml for the compound of Example C-4; 133% and 209% at 30 µg/ml, and 56% and 84% at 10 µg/ml for the compound of Example C-5; 107% and 243% at 10 µg/ml for the compound of Example C-6; 128% and 184% at 100 µg/ml, 99% and 118% at 30 µg/ml, and 45% and 77% at 10 µg/ml for the compound of Example C-7; 229% and 307% at 30 µg/ml, 83% and 107% at 10 µg/ml, and 33% and 44% at 3 µg/ml for the compound of Example C-9; 105% and 177% at 30 µg/ml, 87% and 114% at 10 µg/ml, and 36% and 40% at 3 µg/ml for the compound of Example C-10; 119% and 200% at 30 µg/ml, and 54% and 101% at 10 µg/ml for the compound of Example C-11; 126% and 273% at 100 µg/ml, 85% and 250% at 30 µg/ml, and 48% and 76% at 10 µg/ml for the compound of Example C-12; 96% and 128% at 100 µg/ml, and 49% and 62% at 30 µg/ml for the compound of Example C-13; 77% and 223% at 100 µg/ml, and 38% and 57% at 30 µg/ml for the compound of Example C-14; 52% and 137% at 100 µg/ml for the compound of Example C-15; 85% and 220% at 100 µg/ml, and 42% and 63% at 30 µg/ml for the compound of Example C-16; and, 39% and 148% at 100 µg/ml for the compound of Example C-17.

When tested by said anesthetized dog procedure, the compounds of the invention or said salts thereof at doses of 0.3, 1.0, 3.0 and/or 10 mg/kg administered intravenously were found to cause significant increases, that is, 25% or greater, in cardiac contractile force or cardiac contractility with lower changes in heart rate and blood pressure. For example, the compound of Example C-1 was found to cause respective increases of 38%, 128% and 198% in contractile force (cf) at doses of 0.3, 1.0 and 3.0 mg/kg; the compound of Example C-4 was found to cause respective cf increases of 46%, 75% and 98% at doses of 1.0, 3.0 and 10.0 mg/kg; the compound of Example C-5 was found to cause respective cf increases of 46% and 75% at 0.3 and 1.0 mg/kg; the compound of Example C-9 was found to cause respective cf increases of 28%, 82% and 152% at 0.3, 1.0 and 3.0 mg/kg; the compound of Example C-10 was found to cause respective cf increases of 50% and 70% at 1.0 and 3.0 mg/kg; and, the compound of Example C-11 was found to cause cf increases of 72% and 127% at doses of 1.0 and 3.0 mg/kg.

The present invention includes within its scope a cardiotonic composition for increasing cardiac contractility, said composition comprising a pharmaceutically acceptable carrier and, as the active component thereof, a cardiotonically effective amount of the compound of formula I where Q' is amino or hydrogen and Q is 4(or 3)-hydroxyphenyl, 4(or 3)-pyridinyl or 4(or 3)-pyridinyl having one or two lower-alkyl substituents or said salt thereof. The invention also includes within its scope the method for increasing cardiac contractility in a patient requiring such treatment which comprises administering to such patient said cardiotonic composition providing a cardiotonically effective amount of the said compound of formula I or said salt thereof. In clinical practice said compound will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the compositions, by irradiation or by heating. They can also be manufactured in the form of sterile solid compositions which can be dissolved in sterile water or some other sterile injectable medium immediately before use.

The percentage of active component in the said composition and method for increasing cardiac contractility can be varied so that a suitable dosage is obtained. The dosage administered to a particular patient is variable, depending upon the clinician's judgement using as the criteria: the route of administration, the duration of treatment, the size and condition of the patient, the potency of the active component and the patient's response thereto. An effective dosage amount of active component can thus only be determined by the clinician considering all criteria and utilizing his best judgement on the patient's behalf.

We claim:

1. 2-Q-4-R'-6-Q'-8-R-pyrido[2,3-d]pyrimidin-5(8H)-one having the formula

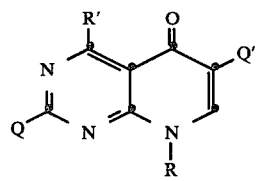

or acid-addition salt thereof, where Q is 4(or 3)-hydroxyphenyl, 4(or 3)-methoxyphenyl, 4(or 3)-pyridinyl or 4(or 3)-pyridinyl having one or two lower-alkyl substituents, R' is hydrogen or alkyl having from one to four carbon atoms, Q' is hydrogen, nitro or amino, and R is alkyl having from one to four carbon atoms, $CH(C_2H_5)_2$, $(CH_2)_nCH=CH_2$ where n is 1 or 2, or Y—Z where Y is alkylene having from two to four carbon atoms and having its connecting linkages on different carbon atoms and Z is hydroxy, $OR_1$ and $NR_1R_2$ where $R_1$ and $R_2$ are each methyl or ethyl.

2. A compound according to claim 1 where Q' is hydrogen or amino, R' is hydrogen or methyl, Q is 4(or 3)-pyridinyl and R is ethyl, n-propyl, n-butyl, allyl, 3-butenyl and 1-ethylpropyl.

3. 8-Ethyl-2-(4-pyridinyl)pyrido[2,3-d]pyrimidin-5(8H)-one according to claim 1 or acid-addition salt thereof.

4. 8-Ethyl-2-(3-pyridinyl)pyrido[2,3-d]pyrimidin-5(8H)-one according to claim 1 or acid-addition salt thereof.

5. 8-Ethyl-2-(4-hydroxyphenyl)pyrido[2,3-d]pyrimidin-5(8H)-one according to claim 1 or acid-addition salt thereof.

6. 8-n-Propyl-2-(4-pyridinyl)pyrido[2,3-d]pyrimidin-5(8H)-one according to claim 1 or acid-addition salt thereof.

7. 8-n-Butyl-2-(4-pyridinyl)pyrido[2,3-d]pyrimidin-5(8H)-one according to claim 1 or acid-addition salt thereof.

8. 8-n-Butyl-2-(3-pyridinyl)pyrido[2,3-d]pyrimidin-5(8H)-one according to claim 1 or acid-addition salt thereof.

9. 6-Amino-8-n-butyl-2-(4-pyridinyl)pyrido[2,3-d]pyrimidin-5(8H)-one according to claim 1 or acid-addition salt thereof.

10. 8-(1-Ethylpropyl)-2-(4-pyridinyl)pyrido[2,3-d]pyrimidin-5(8H)-one according to claim 1 or acid-addition salt thereof.

11. 8-(3-Butenyl)-2-(4-pyridinyl)pyrido[2,3-d]pyrimidin-5(8H)-one according to claim 1 or acid-addition salt thereof.

12. 8-Isopropyl-2-(4-pyridinyl)pyrido[2,3-d]pyrimidin-5(8H)-one according to claim 1 or acid-addition salt thereof.

13. A cardiotonic composition for increasing cardiac contractility, said composition comprising a pharmaceutically acceptable carrier and, as the active component thereof, a cardiotonically effective amount of the compound having the formula

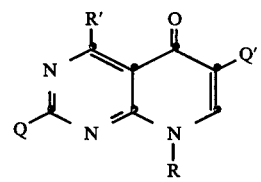

where R' is hydrogen or alkyl having from one to four carbon atoms, and R is alkyl having from one to four carbon atoms, $CH(C_2H_5)_2$, $(CH_2)_nCH=CH_2$ where n is 1 or 2, or Y-Z where Y is alkylene having from two to four carbon atoms and having its connecting linkages on different carbon atoms and Z is hydroxy, OR, or $NR_1R_2$ where $R_1$ and $R_2$ are each methyl or ethyl, Q' is amino or hydrogen and Q is 4(or 3)-hydroxyphenyl, 4(or 3)-pyridinyl or 4(or 3)-pyridinyl having one or two lower alkyl substituents, or pharmaceutically acceptable acid-addition salt thereof.

14. A composition according to claim 13 where the active component is the compound where Q is 4(or 3)-pyridinyl, R' is hydrogen or methyl, Q' is hydrogen or amino, and R is ethyl, n-propyl, n-butyl, allyl, 3-butenyl and 1-ethylpropyl.

15. The method of increasing cardiac contractility in a patient requiring such treatment which comprises administering orally or parenterally in a solid or liquid dosage form to such patient a composition according to claim 13.

16. The method for increasing cardiac contractility in a patient requiring such treatment which comprises administering orally or parenterally in a solid or liquid dosage form to such patient a composition according to claim 14.

* * * * *

UNITED STATES PATENT AND TRADEMARK OFFICE
CERTIFICATE OF CORRECTION

PATENT NO. : 4,432,981
DATED : February 21, 1984
INVENTOR(S) : G.Y. Lesher, B. Singh and S.C. Laskowski It is certified that error appears in the above-identified patent and that said Letters Patent is hereby corrected as shown below:

Column 3, line 59, "acid of" should read -- acid or --.

Column 5, line 33, "(2Q-" should read -- (2-Q- --.

Claim 15, line 1, "of" should read -- for --.

Signed and Sealed this

Tenth Day of September 1985

[SEAL]

Attest:

DONALD J. QUIGG

Attesting Officer      Acting Commissioner of Patents and Trademarks - Designate